(12) United States Patent
Jones et al.

(10) Patent No.: US 9,370,389 B2
(45) Date of Patent: Jun. 21, 2016

(54) BIOLOGIC INJECTION SYSTEM

(71) Applicants: David Bradley Jones, Redding, CA (US); J. Scott Hay, Parkland, FL (US); Ryan Singh, Loxahatchee, FL (US)

(72) Inventors: David Bradley Jones, Redding, CA (US); J. Scott Hay, Parkland, FL (US); Ryan Singh, Loxahatchee, FL (US)

( * ) Notice: Subject to any disclaimer, the term of this patent is extended or adjusted under 35 U.S.C. 154(b) by 138 days.

(21) Appl. No.: 13/666,281

(22) Filed: Nov. 1, 2012

(65) Prior Publication Data
US 2013/0123921 A1    May 16, 2013

Related U.S. Application Data

(60) Provisional application No. 61/554,114, filed on Nov. 1, 2011, provisional application No. 61/598,972, filed on Feb. 15, 2012, provisional application No. 61/649,467, filed on May 21, 2012.

(51) Int. Cl.
*A61B 17/88* (2006.01)
*A61F 2/46* (2006.01)
*A61F 2/30* (2006.01)

(52) U.S. Cl.
CPC ............... *A61B 17/88* (2013.01); *A61F 2/4601* (2013.01); *A61F 2002/30523* (2013.01)

(58) Field of Classification Search
CPC .............. A61F 2/4601; A61B 17/8816; A61B 17/8822
USPC ...................................... 606/93, 94
See application file for complete search history.

(56) References Cited

U.S. PATENT DOCUMENTS

| | | | |
|---|---|---|---|
| 2005/0113762 A1* | 5/2005 | Kay et al. | 604/181 |
| 2006/0149282 A1* | 7/2006 | Vendrely et al. | 606/94 |
| 2008/0281336 A1* | 11/2008 | Zergiebel | 606/142 |
| 2009/0093818 A1* | 4/2009 | Baroud | 606/93 |
| 2009/0204120 A1* | 8/2009 | Trosken et al. | 606/93 |

* cited by examiner

*Primary Examiner* — David Bates
(74) *Attorney, Agent, or Firm* — Laurence A. Greenberg; Werner H. Stemer; Ralph E. Locher

(57) ABSTRACT

A medical compound delivery device, including an elongated compound delivery conduit; a housing attached to the delivery conduit; a dispensing element movably positioned within the housing; an actuation element coupled to the housing, the actuation element operable to selectively move the dispensing element from the housing into the delivery conduit in discrete length increments; and a pressure limiting element configured to limit movement of the dispensing element when a pressure in the delivery conduit exceeds a predetermined threshold pressure.

17 Claims, 9 Drawing Sheets

BIOLOGIC INJECTION SYSTEM

CROSS-REFERENCE TO RELATED APPLICATION

This application is related to and claims priority to U.S. Provisional Patent Application Ser. No. 61/554,114, filed Nov. 1, 2011; U.S. Provisional Patent Application Ser. No. 61/598,972, filed Feb. 15, 2012; and U.S. Provisional Patent Application Ser. No. 61/649,467, filed May 21, 2012; the entirety of all of which is incorporated herein by reference.

STATEMENT REGARDING FEDERALLY SPONSORED RESEARCH OR DEVELOPMENT n/a

FIELD OF THE INVENTION

The present invention relates to methods and systems for preparing and controllably delivering biological, pharmaceutical, and/or other therapeutic or healing materials to a surgical site.

BACKGROUND OF THE INVENTION

In many orthopedic procedures, bone graft material is processed and delivered to a surgical site in order to augment the natural bone. Such graft material typically includes autogenous bone, allograft, xenograft, or synthetic bone graft substitutes. In many orthopedic surgical procedures, particularly joint replacement surgery, certain implantable components must be affixed to bone. A patient's bone quality in an area where a prosthetic component is to be implanted must be sufficient to enable effective anchoring of the prosthesis to the bone. In such situations, bone graft material is used augment the bone. In the case of bone defects or injury, synthetic or natural bone grafts may also be implemented to fix the defect or injury. For example, bone graft materials and methods are used in cavities resulting from tumor removal or significant fractures.

Bone graft procedures are also typically implemented when removing and/or replacing a previously-implanted prosthesis. In such implant revision surgery, a previously implanted prosthesis is removed and replaced with a new prosthesis, and bone graft is used to fill-in or otherwise augment the cavity formed by removal of the previously implanted prosthesis (and any old bone cement, particulate debris, membrane, beads and other remnants associated with the prosthesis) to facilitate secure and desired positioning and implantation of the new prosthesis.

Bone graft may be used in a wet or slurry form, or alternatively, in a dry or particulate/granule form. Moreover, bone graft material may include a range of irregular particle sizes. The present disclosure provides improved systems and methods of use thereof that accurately deliver or dispense bone graft of varying particulate dimensions in a timely and controlled manner to a particular receiving location.

SUMMARY OF THE INVENTION

The present disclosure advantageously provides a medical compound delivery device, including an elongated compound delivery conduit; a housing attached to the delivery conduit; a dispensing element movably positioned within the housing; an actuation element coupled to the housing, the actuation element operable to selectively move the dispensing element from the housing into the delivery conduit in discrete length increments; and a pressure limiting element configured to limit movement of the dispensing element when a pressure in the delivery conduit exceeds a predetermined threshold pressure. The housing may define a handle and the actuation element may include a depressible trigger coupled to the handle. The device may include a planetary gear assembly disposed within the housing and coupled to the actuation element, where the planetary gear assembly is configured to move the dispensing element a pre-set distance per each discrete activation of the actuation element. The device may include a bypass element coupled to the housing and operable to move the dispensing element independently of the actuation element. The dispensing element may include an elongated, flexible cylindrical body, and the pressure limiting element may include a slipper gear assembly coupled to the actuation element. The housing may define a path therein guiding the movement of the dispensing element, and a wheel may be rotatably disposed within the housing, where the dispensing element circumscribes at least a portion of the wheel. The device may include at least one radiopaque marker coupled to at least one of the delivery conduit or housing and a cartridge releasably attachable to the delivery conduit, wherein the cartridge defines a cavity therein for storing a medical compound.

A surgical injection device is provided, including a handle, the handle defining a path therein; a delivery conduit coupled to the handle; a dispensing element movably disposed at least partially within the path, the dispensing element being sized and shaped to be movably positionable within the delivery conduit; and an actuation mechanism coupled to the handle and configured to controllably move the dispensing element along the delivery conduit in pre-set distance increments. The device may include a spool rotatably positioned within the housing, where the dispensing element circumscribes at least a portion of the spool, and a bypass switch coupled to the handle and operable to move the dispensing element independently of the actuation mechanism. The device may include a slipper gear assembly coupled to the actuation mechanism and configured to limit movement of the dispensing element when a pressure in the delivery conduit exceeds a predetermined threshold pressure.

A method of delivering a medical compound to a surgical site is provided, including incrementally advancing a dispensing element through a delivery conduit to expel the medical compound out of the delivery conduit, and limiting the advancement of the dispensing element when a pressure within the delivery conduit exceeds a pre-selected pressure threshold. The surgical site may include a portion of a spinal segment, incrementally advancing the dispensing element may be achieved at least in part by actuating a gear assembly to move the dispensing element along the delivery conduit in pre-set distance increments, and/or limiting the advancement of the dispensing element may be achieved at least in part through operation of a slipper gear assembly. The method may include attaching a cartridge to the delivery conduit, where the cartridge contains the medical compound therein.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
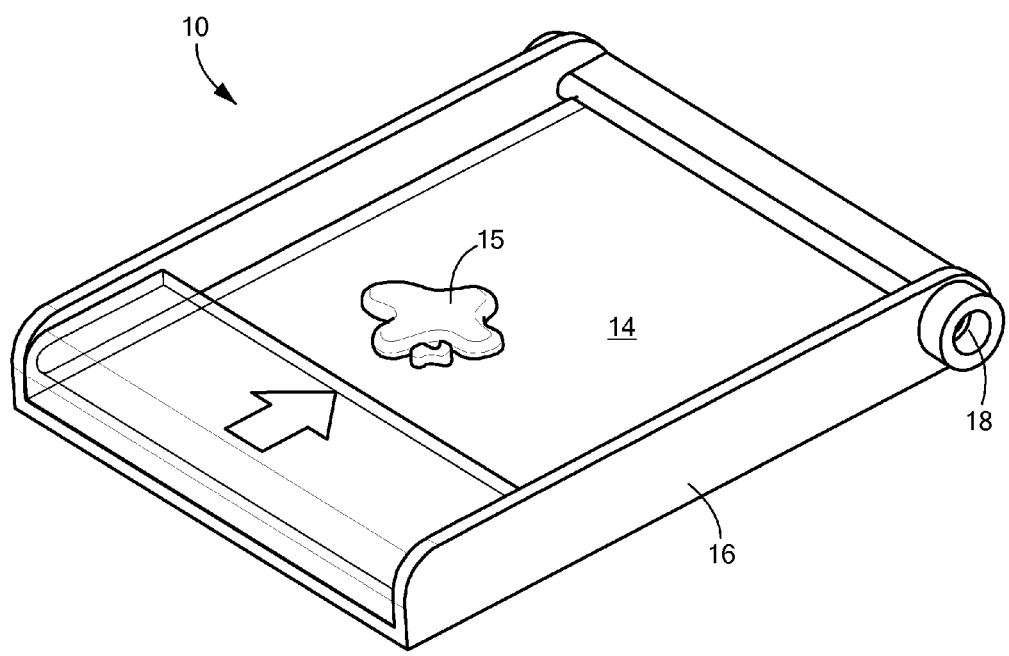
FIG. 1 shows an example of a biological material preparation and loading system constructed in accordance with the principles of the present disclosure

The present invention provides systems and methods of use thereof for accurately preparing and delivering or dispensing biological, pharmaceutical, or other therapeutic or medical materials in a timely and controlled manner to a particular receiving location. In a particular example, the systems and methods of use described herein may include the preparation and delivery of bone graft materials or compounds to an orthopedic and/or spinal surgical site. Referring now to the drawing figures in which like reference designations refer to like elements, an example of a biological material preparation and loading system 10 is shown in FIGS. 1-4, and an example of a biological material delivery system 12 is illustrated in FIGS. 5-9.

Figure 2:
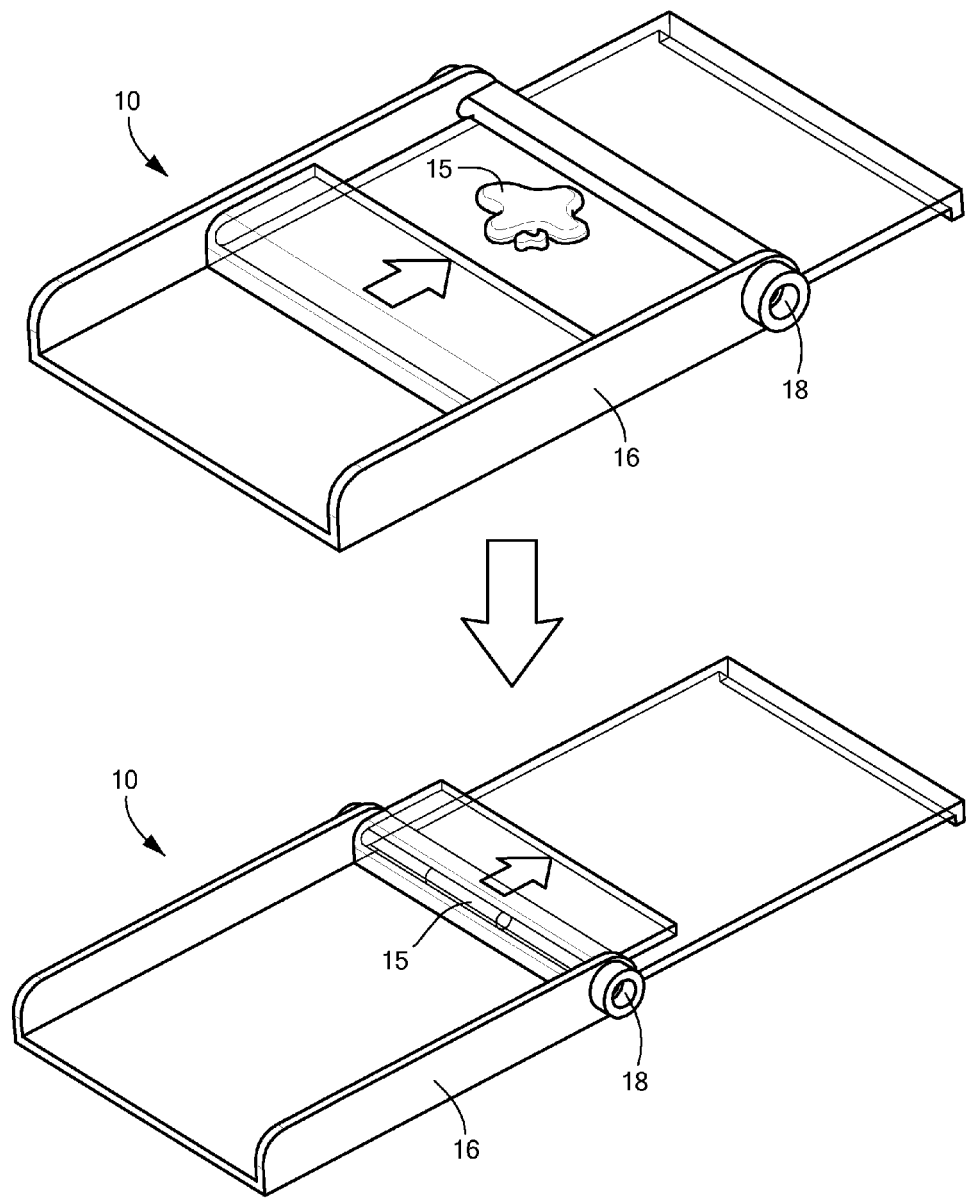
FIG. 2 illustrates a method of using the biological material preparation and loading system of FIG. 1.
Figure 3:
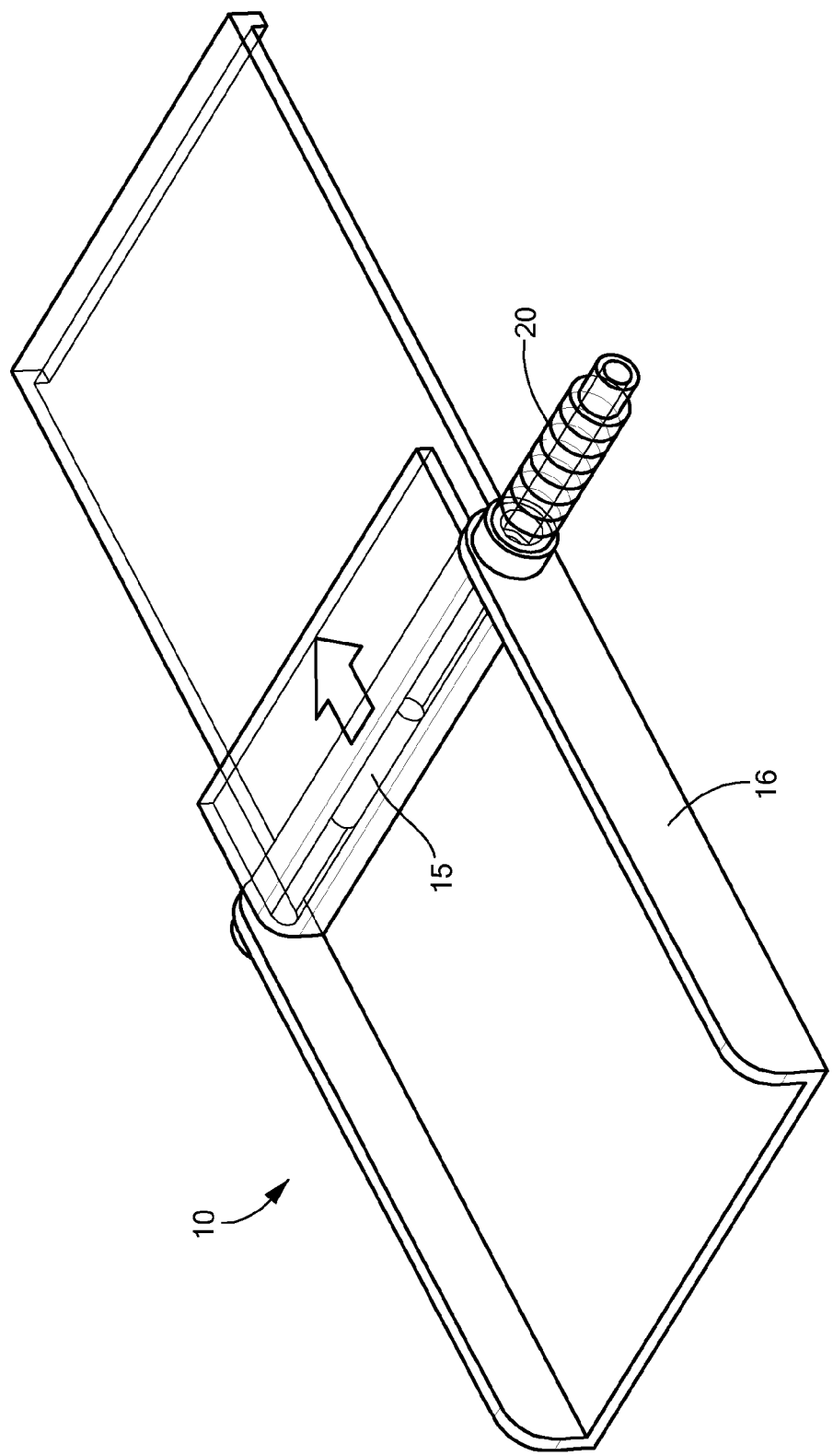
FIG. 3 is another illustration of a method of using the biological material preparation and loading system of FIG. 1.
Figure 4:
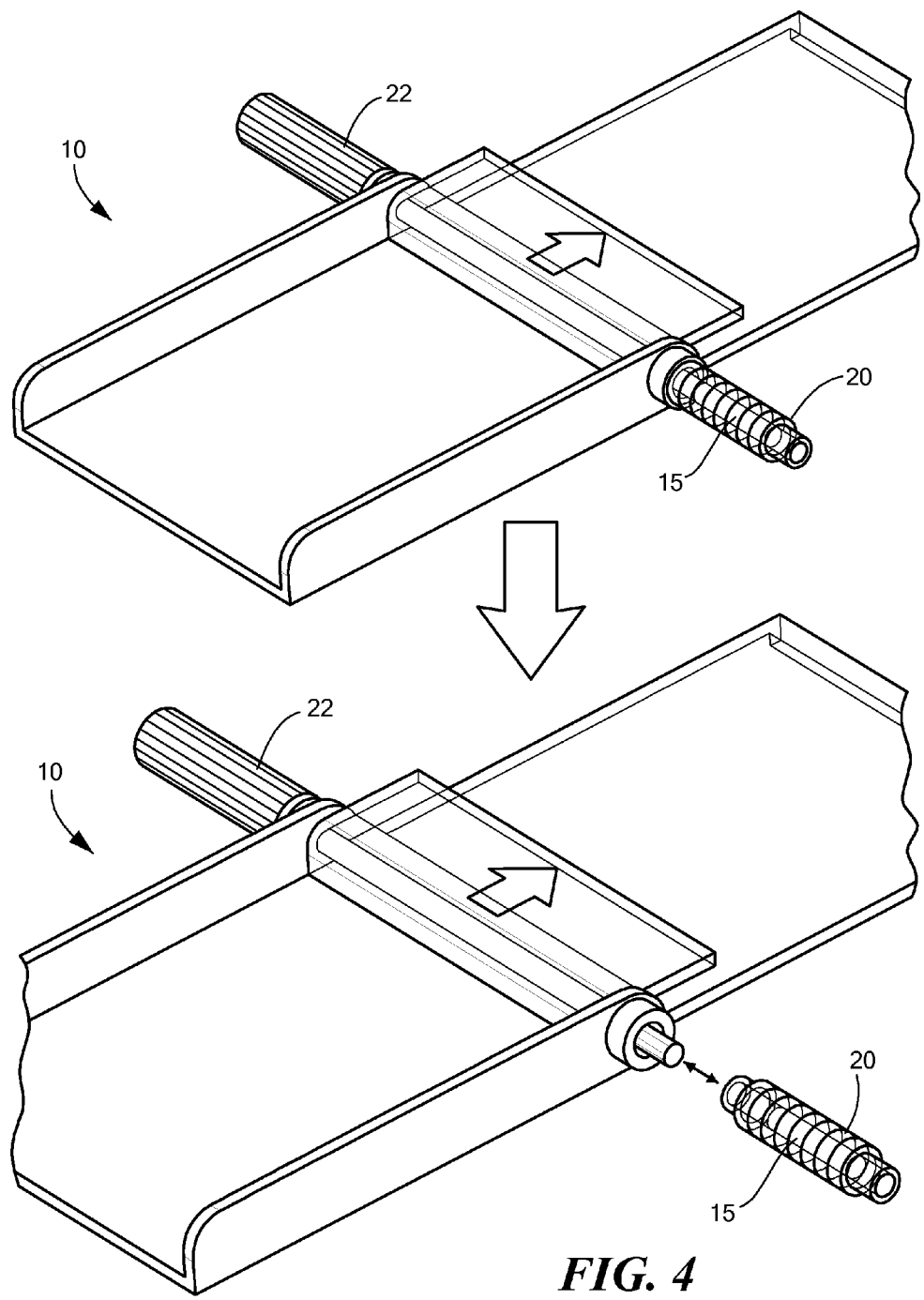
FIG. 4 is an additional illustration of a method of using the biological material preparation and loading system of FIG. 1.
Figure 5:
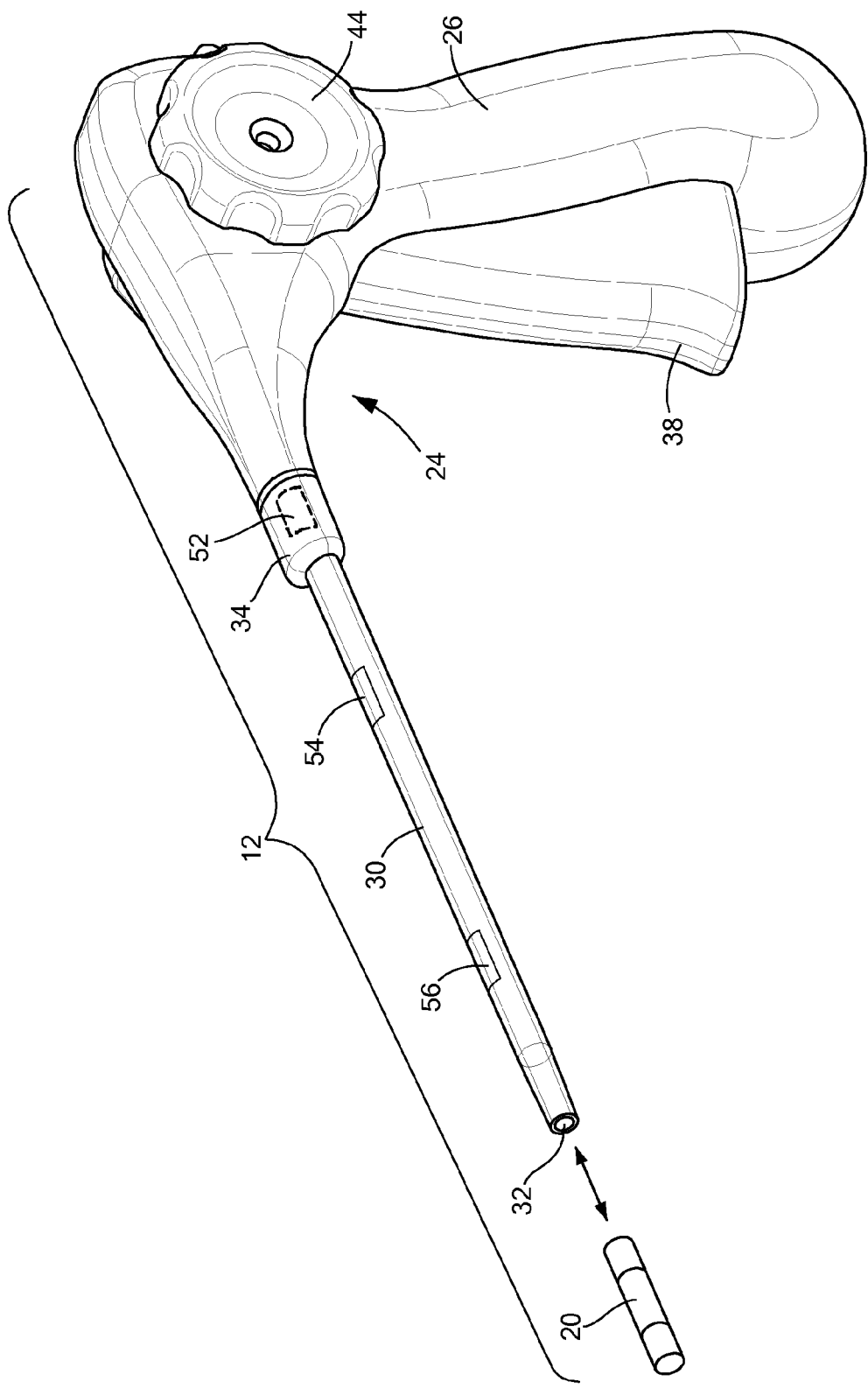
FIG. 5 is an illustration of a front perspective view of an example of a biological material delivery device constructed in accordance with the principles of the present disclosure.
Figure 6:
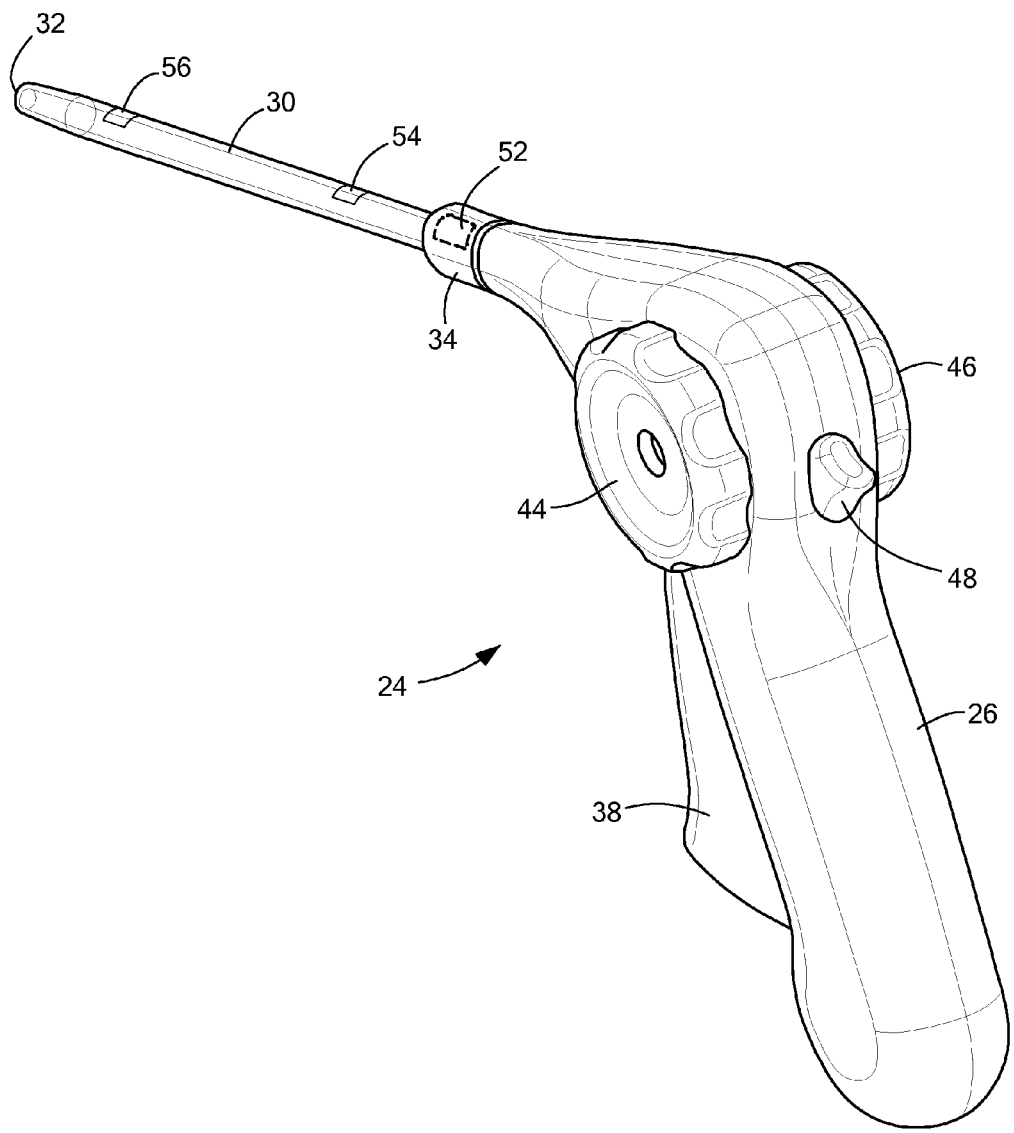
FIG. 6 is an illustration of a rear perspective view of the biological material delivery device of FIG. 5.
Figure 7:
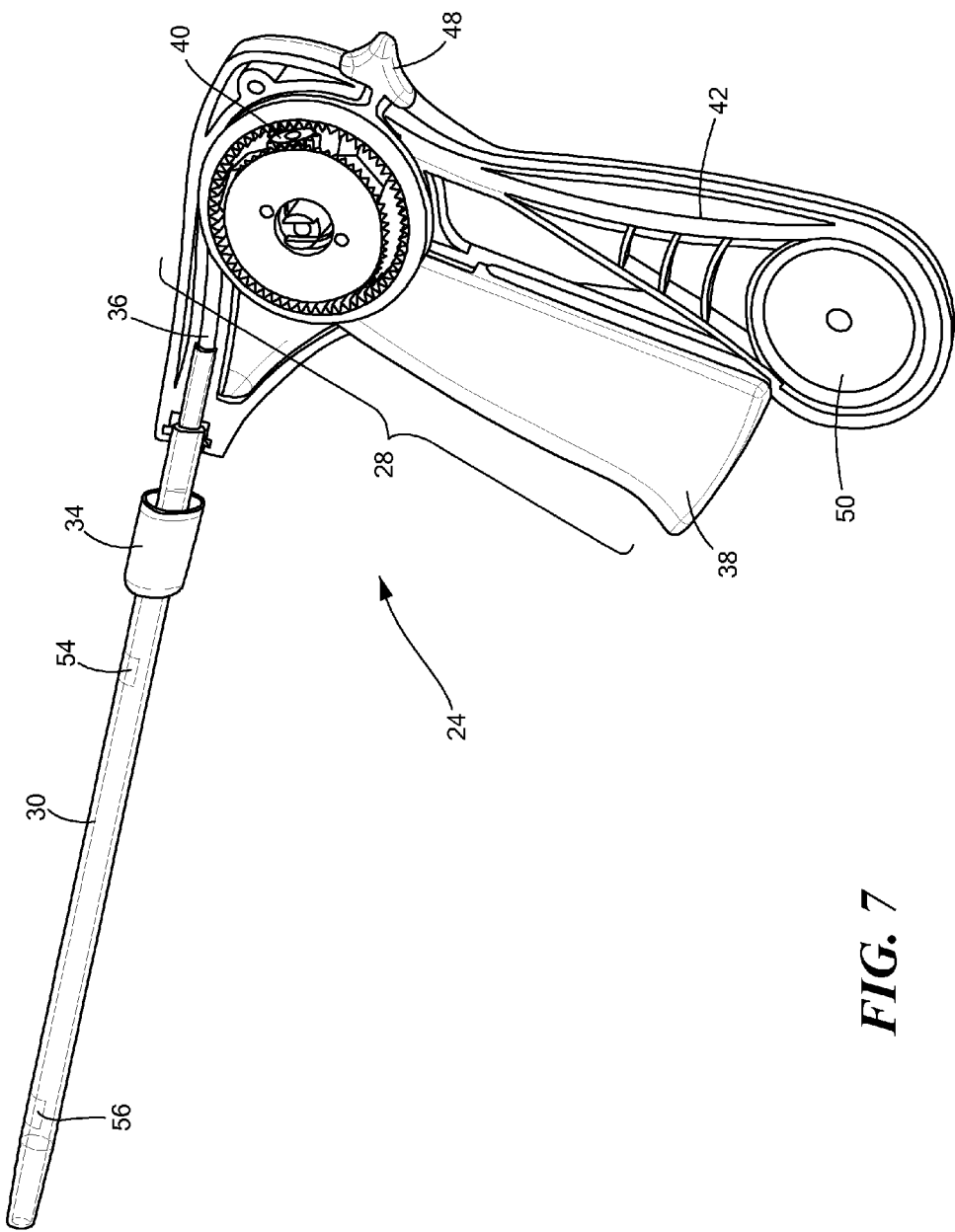
FIG. 7 is an illustration of an interior portion of the biological material delivery device of FIG. 5.
Figure 8:
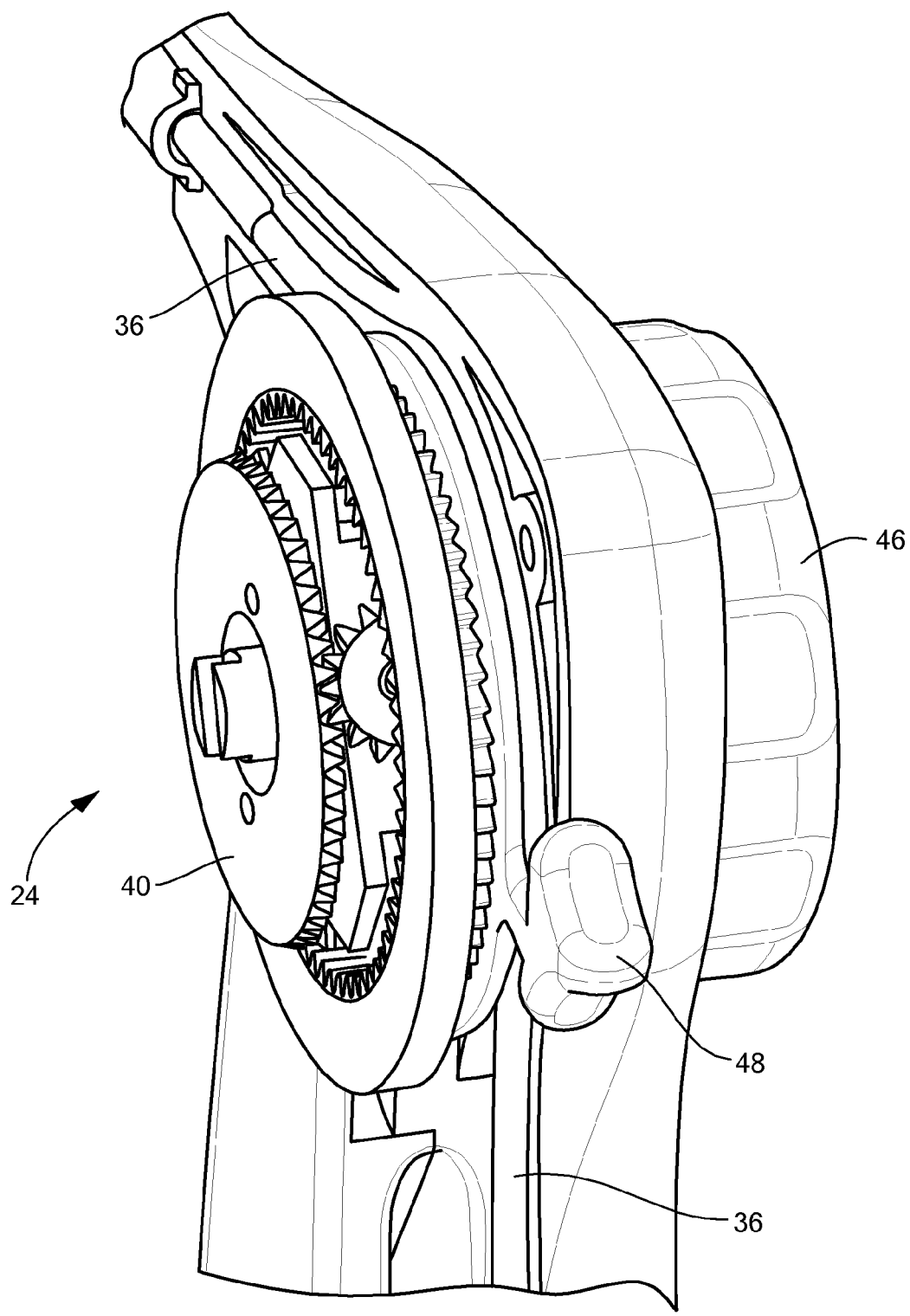
FIG. 8 is another illustration of an interior portion of the biological material delivery device of FIG. 5.
Figure 9:
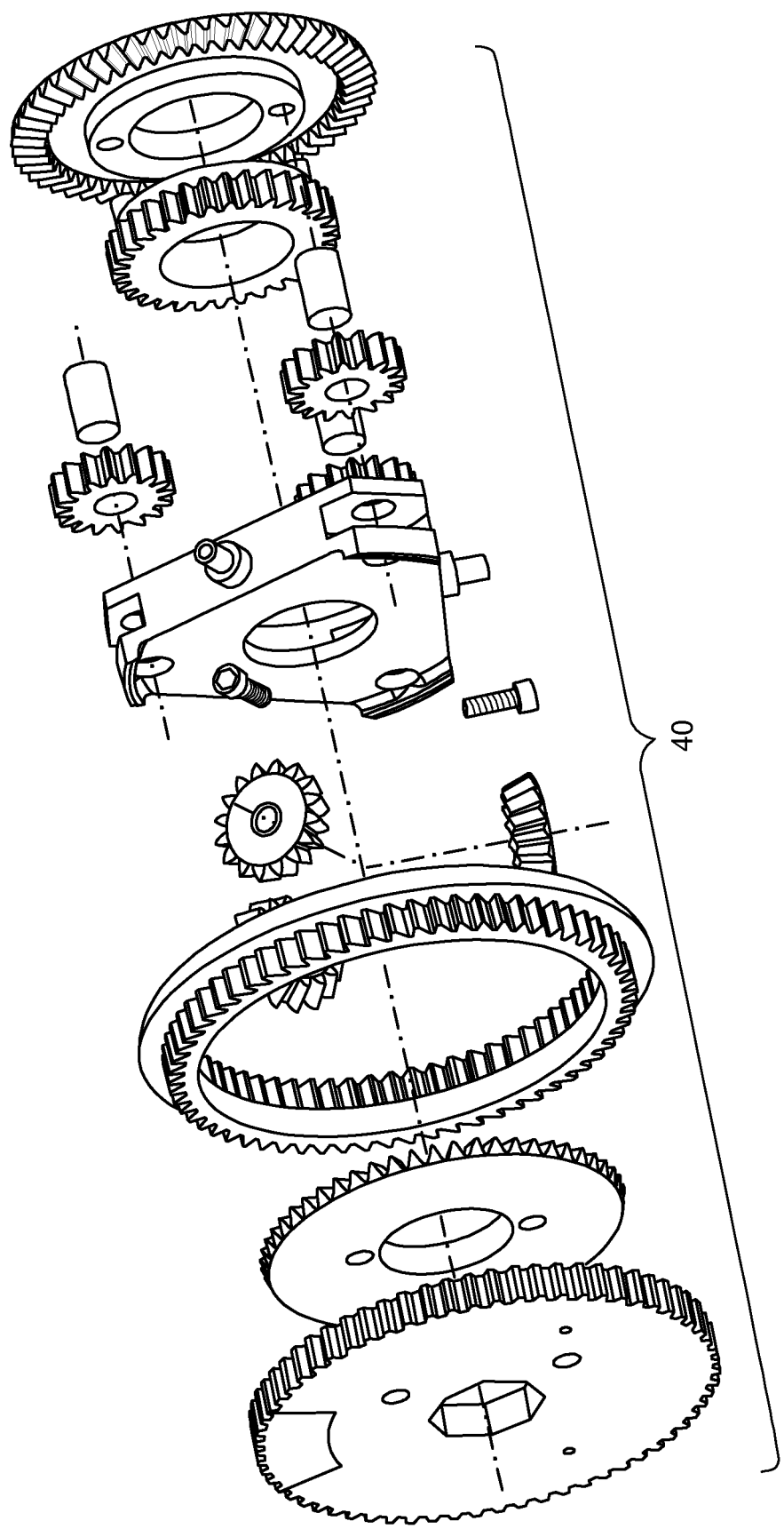
FIG. 9 is an exploded-view illustration of an example of a gear assembly of the biological material delivery device of FIG. 5.

Now referring to FIG. 1, the preparation and loading system 10 generally defines a specimen or material receiving area 14 of sufficient size and area to receive a quantity or volume of material 15, whether biological, pharmaceutical, combinations thereof, or the like, to be inserted or otherwise dispersed within a surgical or medical site of a patient. As shown in FIG. 2, the receiving area 14 may be movably disposed about a frame 16 to direct the material 15 towards a loading passage 18, which may compress, shape, or otherwise collect the material 15 into a consolidated volume. A material or specimen cartridge 20 may be releasably engageable with the loading passage 18, and a loading tool or other actuation mechanism 22 may be movably directed into the loading passage 18 to move the specimen or materials 15 from the loading passage 18 into the cartridge 20, as shown in FIGS. 3-4. A plurality of cartridges having varying volumes may be provided to address different procedures having varying needs for the prepared biological specimen or materials. The now-loaded cartridge 20 containing the prepared volume of materials 15 may then be detached from the loading passage 18 (as shown in FIG. 4) and coupled to the delivery system 12 to dispense or deliver the loaded materials to the desired site, as described in more detail below. The cartridge may include one or more releasable caps or lids (not shown) to prevent spillage or leakage of the materials 15 when transitioning from the preparation and loading system 10 to the delivery system 12.

Now turning to FIGS. 5-9, the delivery system 12 generally includes a selectively controllable mechanism to accurately dispense desired amounts of the prepared specimen or materials from the loaded cartridge 20 to a tissue site. The delivery system 12 generally may include a delivery device 24 defining a housing and/or graspable handle 26 and an actuation mechanism 28 attached to the handle 26. The delivery system 12 may include pairing the delivery device 24 with the cartridge 20 for use in a medical procedure.

The device 24 may define a chamber for receiving the cartridge 20, and a delivery conduit or channel 30 leading from the cartridge to a distal tip 32 where the processed, prepared materials will exit the device 24. Alternatively, the cartridge 20 may couple directly to the handle 26 and/or a body or housing of the device 24 at one end, and the delivery conduit or passage 30 may then couple to an opposite end of the cartridge 20. In another example, the cartridge 20 may be releasably coupled directly to the distal tip 32 of the delivery conduit 30. The releasable engagement may be achieved through the matable interlocking of one or more complimentary features on the distal tip 32 and the cartridge 20 to sufficiently secure the cartridge 20 to the delivery device 24 for subsequent use in a surgical procedure.

The delivery conduit 30 may be flexible and/or malleable to take on varying shapes or configurations to facilitate use of the device. For example, though illustrated as a substantially linear, straightened conduit, the delivery conduit may be arcuate along one or more portions of its length. Varying degrees of curvature may be implemented to facilitate entry and positioning into small surgical spaces. In addition, a plurality of selectable delivery conduits may be provided with the device 24 to enable its use in a variety of different surgical sites having varying dimensions or tortuous routes leading to region where the graft or tissue material is desired. The delivery conduit 30 may further be constructed of a transparent or translucent material to allow visual confirmation and monitoring of graft material or other medical compound(s) traveling down the conduit and towards the delivery area. The delivery conduit and/or a portion of the cartridge may be porous or moisture permeable to allow the infusion or removal of additional materials to the material 15 to be inserted. For example, excess moisture in the material 15 may be extricated through the delivery conduit 30 and/or the cartridge 20. Alternatively, one or more materials, such as pharmaceutical or other medical compounds, may be introduced through a porous portion of the delivery conduit 30 and/or cartridge 20.

The device may include a strain relief or support component 34 at a junction between the delivery conduit 30 and a portion of the handle 26 and/or housing of the device 24. For example, the relief component may include a conical segment circumscribing a portion of the delivery conduit 30 to bolster, support, or otherwise counteract stresses or strains at the junction. The strain relief 34 may minimize or reduce the likelihood that the delivery conduit 30 kinks, breaks, or is otherwise damaged during use. During use, forces applied or experienced at a distal end of the delivery conduit 30 may result in large torques or forces at the proximal end of the delivery conduit closer to the handle and/or device body.

The distal tip 32 may provide a directional opening or outlet to disperse the materials 15 in a desired direction or orientation upon exiting the device. For example, the distal tip 32 may provide a tapered or curved opening directing material in one or more pre-selected directions with respect to a longitudinal axis of the delivery conduit 30 and or the patient (e.g., cranially, caudally, anteriorly, posteriorly, etc.). The distal tip 32 may further be matable or engageable with a feature on an implanted prosthesis to deliver contents into an interior cavity or passage of the prosthesis. Substantially sealing or coupling the distal tip 32 to a feature, such as a port or opening in a prosthesis (not shown) aids in avoiding overflow or leakage of delivered material exterior to the prosthesis, and may also substantially preserve the pressure head of the graft or other material being delivered through the delivery system 12. To facilitate the sealing or engagement, the distal tip 32 may include, for example, a tapered sealing tab, flap geometry, and/or an "O-Ring" type of interface employing implant grade silicones that can elastically mate into openings provided by the prosthesis and seal off the "nozzle-implant" interface from leaking biologic product when under internal pressure. The substantially sealed engagement between the delivery system 12 and the prosthesis may also facilitate the introduction of fluids or pressure to expand or deploy a portion of an expandable prosthesis (such as a laterally and/or vertically expandable fusion cage, or the like).

The distal tip 32 may have a myriad of different shapes and sizes to deliver the biological material to a surgical site which may include, for example, one or more implanted prostheses having cavities or regions therein for receiving the material 15. Particular examples of distal tip geometry may include funneled or tapered diameter tips; a dispersion port having a rectangular or square-like cross section; and/or angled bend or directional curve forming an angle with respect to a longitudinal axis of the delivery conduit 30. The variations in the distal tip geometry described above may optionally be applied to a portion of the cartridge 20 in the event the cartridge is attached directly to the distal tip 32 for subsequent delivery to a surgical site The device 24 may further include a dispensing element 36 movably positioned within the delivery device 24, and controllably movable into and out of the delivery conduit 30 for the controlled expulsion of a medical compound from the device 24. The dispensing element may include an elongated, flexible body or cable that is sized and/or shaped to function as a plunger within the delivery conduit 30. The dispensing element may, for example have a cylindrical shape and/or rounded cross section substantially similar to the cross section of the delivery conduit 30.

The dispensing element 36 may be coupled to the actuation mechanism 28 such that manipulation or operation of the actuation mechanism 28 results in the controlled movement of the dispensing element 36 towards the cartridge 20 and/or distal tip of the delivery conduit 30. The dispensing element 36 then proceeds into and through the cartridge 20 to move the loaded materials 15 out of the cartridge 20 and either into the delivery conduit 30 towards the distal tip 32, or out of the cartridge and into the surgical site (depending on the particular configuration selected). The actuation mechanism 28 may be configured and operable to selectively move the dispensing element 36 from the housing or body of the delivery device 24 (which may include the handle 26) into the delivery conduit 30 in discrete length increments For example, the actuation mechanism 28 may include an actuation element 38 operably coupled to the handle 26. The actuation element 38 may include, for example, a depressible trigger. The actuation mechanism may further include one or more gear assemblies 40 mechanically linking the actuation element 38 to the dispensing element 38 for the controlled movement thereof. The dispensing element 36 may include, for example, a flexible elongate body having a plurality of depressions or grooves therein that matably couple to one or more of the gears of the gear assemblies 40, such that turning of the gears directs the dispensing element 36 through a channel or passage 42 in the device 24 and towards the cartridge 20 and/or delivery conduit 30. Alternatively, the dispensing element 30 may be substantially smooth and may interact with the actuation mechanism 28 through compression or friction to controllably move the dispensing element 36 as desired.

Manipulation of the actuation element 38 may in turn actuate the gear assembly 40 to rotate a predetermined number of steps or radial distance. The radial distance that the gear assembly 40 turns may translate to a predetermined, discrete length of movement for the dispensing element 36, resulting in a predictable expulsion of a known amount or volume of the medical compound or material from the system 12.

The actuating mechanism 28 may include both large volumetric delivery control or movement of the dispensing element 36 as well a finer control mechanism to aid in delivering precisely the desired amount of tissue to a surgical site. For example, the actuating mechanism 28 may include a first control or knob 44 that moves the dispensing element 36 in larger increments, while the actuation element and one or more secondary gears and/or controls 46 provide precise movement of the dispensing element 36 and resulting compound delivery in smaller, more-precise quantities.

The actuating mechanism 28 may further include an override or bypass mechanism operable to advance or retract the dispensing element 36 independently of the actuation element 38 and/or the actuation mechanism 28 when desired. For example, the device 24 may include a bypass switch 48 coupled to the handle 26 that is selectively operable to disengage the dispensing element from the one or more gear assemblies 40. In a first position, the bypass switch may allow the first and/or second knobs 44, 46 to be used to advance or retract the dispensing element 36 as desired without being limited to the incremental lengths provided through operation of the actuation mechanism 28. In a second position, the bypass switch may couple the dispensing element 36 to the actuation mechanism 28 for controlled, incremental advancement or retraction.

As mentioned above, the device 24 may include or define a channel or path 42 for the dispensing element 36. The path 42 may extend or traverse the interior of the handle 26, for example, to maintain a compact profile and to prevent the dispensing element 36 from kinking or snagging other interior components of the device 24. The device 24 may include a wheel or spool 50 rotatably positioned within or otherwise coupled to the handle 26. The wheel 50 may be positioned proximate the defined path 42 such that the dispensing element 36 circumscribes or is wrapped around a portion of the wheel 50. The wheel 50 thus facilitates movement of the dispensing element 36 through the path when the device is in use.

The delivery system 12 may be torque and/or pressure limiting to prevent over pressurization of the delivered materials into the surgical site. Growth factors found in bone products (i.e. autograft, stem cells, etc) can be negatively affected when pressurized, and accordingly, the delivery system may operably prevent pressures from exceeding a predetermined or preselected threshold, which may be selectable in the range between approximately 40 psi and 80 psi, for example. Excessive pressures may also result from and/or indicate an obstruction in the device or at the surgical site. The delivery system may include one or more mechanisms for alerting and/or preventing pressures above a selected level. For example, the delivery system 12 may include one or more pressure sensors 52 on or about the actuation mechanism 28 and/or the delivery conduit 30 that detect pressure levels within the device 24. The sensors may be in communication with a visual, audible, and/or tactile alert mechanism (not shown) to signal the user that pressure levels are approaching or exceeding a threshold.

The delivery device 24 may also include one or more vents or over-pressurization outlets 54 to allow any entrained air in the device to escape rather than be introduced into the targeted tissue site. The one or more vents may further provide a valve that opens to allow excess material to exit the device when a pressure threshold has been met or exceeded. The one or more vents or valves may be positioned in fluid communication with the delivery conduit 30 and/or cartridge 20. The one or more vents or valves may, for example, be located in the handle 26, at one or more positions along the length of the delivery conduit 30, and/or at a junction between the cartridge 20 and the delivery conduit 30 and/or handle 26.

The delivery system 12 may include one or more mechanisms preventing pressures from exceeding a threshold during operation of the device. For example, the delivery system may include a clutch or slipper gear assembly as part of the one or more gear assemblies 40. The clutch or slipper gear assembly may include one or more friction plates, pulleys, springs, torque pins, or the like as known in the art, that prevent operation of the delivery system 12 when a pressure or torque threshold is exceeded. For example, the clutch or slipper gear assembly may prevent torque transfer from the actuation mechanism 28 to the dispensing element 36 when the threshold is exceeded.

The device 24 may include one or more mechanisms that limit the travel or movement of the dispensing element 36 within a portion of the device, such as the delivery conduit 30 and/or the cartridge 20 to prevent the dispensing element 36 from extending into the surgical site. For example, the dispensing element 36 may include one or more notches or grooves that are matable with and/or correspond to a protrusion or latch on the device 24 that prevent the dispensing element 36 from moving past a certain point or traveling beyond a certain, predetermined length. The latch/groove mechanism may be selectively engaged and/or disengaged by a user to override the preventative measure and/or to retract the dispensing element.

The delivery system 12 may also include one or more markers 56 to aid in imaging or tracking of the delivery system during a procedure. The markers may include, for example, passive spheres that are attachable and removable from one or more components of the delivery system. Alternatively, the markers 56 may be powered or active to transmit location information and/or respond to stimulation signals for position information and/or triangulation, including radiofrequency signals, impedance measurements, or the like. The markers 56 may be radiopaque for use under fluoroscopy.

In an exemplary method of use of the systems and devices described herein, a prepared medical compound is controllably delivered to a medical or surgical site, such as an intervertebral space or prosthesis, a portion of a spinal segment, or other orthopedic location. The medical compound may be inserted into the cartridge 20 using the preparation and loading system 10 described herein. The cartridge 20 may then be coupled to the delivery device 24. The delivery conduit 30 and/or the cartridge 20 may be positioned proximate to the surgical site, and the delivery device may be operated to incrementally advance the dispensing element 36 through the delivery conduit 30 to abut and then expel the medical compound out of the delivery conduit 30 and/or cartridge 20. The incremental advancement of the dispensing element 36 may be achieved at least in part by actuating the actuation element 38 and/or one or more of the gear assemblies 40 to move the dispensing element along the delivery conduit in pre-set distance increments. Alternatively, the bypass switch 48 may be activated for substantially uninhibited manual control of the advancement and retraction of the dispensing element 36.

The advancement of the dispensing element 36 may be limited when a pressure within the delivery conduit 30 exceeds a pre-selected pressure threshold. The pressure limiting may be achieved through the use of one or more pressure and/or torques limiting mechanisms and features described herein.

It will be appreciated by persons skilled in the art that the present invention is not limited to what has been particularly shown and described herein above. In addition, unless mention was made above to the contrary, it should be noted that all of the accompanying drawings are not to scale. Of note, the system components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein are not necessarily exclusive of each other and may be included in a variety of different combinations or configurations without departing from the scope and spirit of the invention. A variety of modifications and variations are possible in light of the above teachings without departing from the scope and spirit of the invention, which is limited only by the following claims.

What is claimed is:

1. A medical compound delivery device, comprising:
   an elongated compound delivery conduit;
   a housing attached to the delivery conduit;
   a dispensing element movably positioned within the housing;
   an actuation element coupled to the housing, the actuation element operable to selectively move the dispensing element from the housing into the delivery conduit in discrete length increments;
   a pressure limiting element configured to limit movement of the dispensing element when a pressure in the delivery conduit exceeds a predetermined threshold pressure; and
   said actuation element including at least one gear assembly and said pressure limiting element interacting with said at least one gear assembly to prevent torque transfer from the actuation element to the dispensing element when the pressure in the delivery conduit exceeds the predetermined threshold pressure.

2. The medical compound delivery device of claim 1, wherein the housing defines a handle.

3. The medical compound delivery device of claim 2, wherein the actuation element includes a depressible trigger coupled to the handle.

4. The medical compound delivery device of claim 1, further comprising a planetary gear assembly disposed within the housing and coupled to the actuation element, wherein the planetary gear assembly is configured to move the dispensing element a pre-set distance per each discrete activation of the actuation element.

5. The medical compound delivery device of claim 1, further comprising a bypass element coupled to the housing and operable to move the dispensing element independently of the actuation element.

6. The medical compound delivery device of claim 1, wherein the dispensing element includes an elongated, flexible cylindrical body.

7. The medical compound delivery device of claim 1, wherein housing defines a path therein guiding the movement of the dispensing element.

8. The medical compound delivery device of claim 7, further comprising a wheel rotatably disposed within the housing, wherein the dispensing element circumscribes at least a portion of the wheel.

9. The medical compound delivery device of claim 1, further comprising at least one radiopaque marker coupled to at least one of the delivery conduit or housing.

10. The medical compound delivery device of claim 1, further comprising a cartridge releasably attachable to the delivery conduit, wherein the cartridge defines a cavity therein for storing a medical compound, the cartridge configured to permit the dispensing element to proceed into and through said cavity to move the medical compound out of the cartridge.

11. A surgical injection device, comprising:
a handle, the handle defining a path therein;
a spool rotatably positioned within the handle, proximate to said path;
a delivery conduit coupled to the handle;
a dispensing element wrapped around said spool and movably disposed at least partially within the path, the dispensing element being sized and shaped to be movably positionable within the delivery conduit;
an actuation mechanism coupled to the handle and configured to controllably move the dispensing element along the delivery conduit in pre-set distance increments;
a cartridge releasably coupled to the delivery conduit, wherein the cartridge defines a cavity therein for storing a medical compound; and
the cartridge configured to permit the dispensing element to proceed into and through said cavity to move the medical compound out of the cartridge.

12. The surgical injection device of claim 11, further comprising a bypass switch coupled to the handle and operable to move the dispensing element independently of the actuation mechanism.

13. The surgical injection device of claim 11, further comprising a pressure limiting element configured to limit movement of the dispensing element when a pressure in the delivery conduit exceeds a predetermined threshold pressure.

14. A method of delivering a medical compound to a surgical site, comprising:
providing a medical compound delivery device according to claim 1;
incrementally advancing a dispensing element through a delivery conduit to expel the medical compound out of the delivery conduit,
and limiting the advancement of the dispensing element when a pressure within the delivery conduit exceeds a pre-selected pressure threshold.

15. The method of claim 14, wherein the surgical site includes a portion of a spinal segment.

16. The method of claim 14, wherein incrementally advancing the dispensing element is achieved at least in part by actuating a gear assembly to move the dispensing element along the delivery conduit in pre-set distance increments.

17. The method of claim 14, further comprising attaching a cartridge to the delivery conduit, the cartridge containing the medical compound therein.

* * * * *